United States Patent [19]

Rogier

[11] 4,356,128

[45] Oct. 26, 1982

[54] FATTY POLYHYDRIC ALCOHOLS HAVING A POLAR FUNCTIONAL GROUP

[75] Inventor: Edgar Rogier, Minnetonka, Minn.

[73] Assignee: Henkel Corporation, Minneapolis, Minn.

[21] Appl. No.: 257,674

[22] Filed: Apr. 27, 1981

[51] Int. Cl.$^3$ ............................................ C07C 121/34
[52] U.S. Cl. ............................. 260/465.6; 260/465.1; 528/60; 528/65; 528/85
[58] Field of Search ....................................... 260/465.6

[56] References Cited

U.S. PATENT DOCUMENTS

| | | | |
|---|---|---|---|
| 2,615,915 | 10/1952 | Ladd | 260/465.6 X |
| 2,712,558 | 7/1955 | Vander Wal et al. | 260/465.6 X |
| 2,818,434 | 12/1957 | Vander Wal et al. | 260/465.6 X |
| 3,119,848 | 1/1964 | Wrigley et al. | 260/465.6 X |
| 3,450,741 | 6/1969 | Becke et al. | 260/465.6 X |
| 3,520,914 | 7/1971 | Kuper | 260/465.6 |
| 4,093,637 | 6/1978 | Miller et al. | 260/405 |
| 4,216,343 | 8/1980 | Rogier | 568/451 X |

*Primary Examiner*—Joseph Paul Brust
*Attorney, Agent, or Firm*—Forrest L. Collins

[57] ABSTRACT

The present invention deals with obtaining fatty alcohols which have polar groups located on the molecule. The fatty alcohols and polyhydric and present excellent vehicles for wetting pigments in coating compositions and paints.

9 Claims, No Drawings

FATTY POLYHYDRIC ALCOHOLS HAVING A POLAR FUNCTIONAL GROUP

BACKGROUND OF THE INVENTION

1. Field of the Invention

This invention describes products containing more than one hydroxyl functionality and in addition thereto, a polar group.

2. Description of the Art Practices

It is now known from this author's work that certain polyhydric alcohols, particularly those having a geminal-bis(hydroxymethyl) functionality are highly useful for curing urethane compositions. Such work is described in the U.S. Pat. Rogier No. 4,216,343 issued Aug. 5, 1980. Such compounds are geminal-bis(hydroxymethyl) alcohols which also contain a terminal hydroxyl functionality. An example of such material is gem-bis(hydroxymethyl) octadecanol.

It has been found highly desirable to use such compounds due to the high reactivity of the hydroxyl groups and the stability of the polyol. Additional work concerning such materials is shown in a series of articles from the Northern Regional Research Laboratory of the U.S. Department of Agriculture at Peoria, Ill. Representative of such materials worked on by the NRRL in obtaining 9,9(10,10)-bis(hydroxymethyl) octadecanoate esters and the corresponding acid. Such work is described by Miller and Pryde [J. Amer. Oil Chemists Soc. 54, 822A–885A (1977); ibid, 55, 469–470 (1978); U.S. Pat. No. 4,093,637]. Further disclosures of hydroformylation technology are an article entitled *Obtention of De Derives Biofunctionnels* found by R. Lai in Rêv. Fr. Corps Gras. 17:455 (1970).b.

Such compounds, however, have carboxyl groups or hydrolyzable ester groups and are thus not fully usable for wetting pigments in polyurethane coatings. Furthermore, compounds such as are disclosed in this invention are miscible with polyisocyanates used to formulate coating systems. It is, of course, necessary to have sufficient miscibility to allow the formulations of the polyhydroxy compounds of the present invention into polyurethanes. Of course, the compounds of the present invention may be utilized in any area where both a polyhydroxyl functionality and a polar group are required.

Throughout the specification and claims, percentages and ratios are by weight, pressure is gauge, and temperatures are in degrees Celsius unless otherwise indicated.

SUMMARY OF THE INVENTION

The present invention describes polyhydroxymethyl compounds containing a polar group which have the formula:

$$CH_3(CH_2)_m[C(CH_2OH)X]_n(CH_2)_p[C(CH_2OH)X]_q(CH_2)_r[C(CH_2OH)X]_s(CH_2)_tCH_2M$$

and mixtures thereof wherein X is either hydrogen or hydroxymethyl but not mixtures thereof provided that there are at least two hydroxymethyl groups per molecule; n plus q plus s are integers the sum of which is from 1 to 3; n, q and s are 0 or 1; m through t are integers the sum of which is from 11 to 19; and M is CN.

DETAILED DESCRIPTION OF THE INVENTION

The present invention as previously noted deals with polyhydroxyl materials which contain a polar functional group which may be introduced into the molecule in one of several methods. The hydroxyl functionality is introduced into the molecules by utilizing an unsaturated material which is hydroformylated utilizing synthesis gas to introduce a formyl group at the site of the unsaturation. Catalysts may be selected such that a polyunsaturated material is either polyhydroformylated or is monohydroformylated. Rhodium catalysts give products which introduce the formyl group at substantially every location of unsaturation in the molecule. Whereas, cobalt catalysts introduce a formyl group only at one site of unsaturation in conjugated polyunsaturated materials.

The formyl groups can then be reacted via a Tollens' reaction utilizing a strong base and two moles of formaldehyde per mole of the original formyl group to convert the formyl group directly to the geminal-bis(hydroxymethyl) structures.

If, however, it is desired, the formyl group may be converted with selective catalysts such as sodium borohydride to convert the formyl group to a hydroxymethyl group. It is noted, however, that the present invention requires that if such a reaction is conducted that the intermediate aldehyde must contain more than one formyl group to ensure that a polyhydroxymethyl compound will be obtained.

The starting materials which may be converted into the desired products of this invention include oleonitrile, an item of commerce. The reactions are shown in the following scheme:

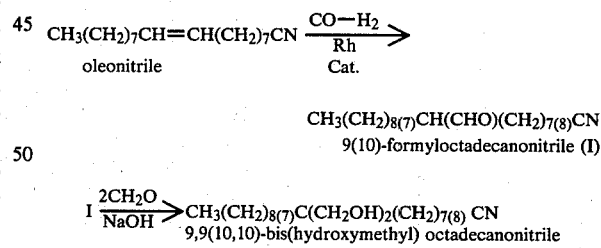

$$CH_3(CH_2)_{8(7)}CH(CHO)(CH_2)_{7(8)}CN$$
9(10)-formyloctadecanonitrile (I)

$$I \xrightarrow[NaOH]{2CH_2O} CH_3(CH_2)_{8(7)}C(CH_2OH)_2(CH_2)_{7(8)} CN$$
9,9(10,10)-bis(hydroxymethyl) octadecanonitrile In a similar fashion, linoleonitrile can be converted into a tetrahydroxynitrile or a dihydroxy nitrile as shown in the following scheme:

$$CH_3(CH_2)_4CH=CH\ CH_2CH=CH(CH_2)_7CN$$

linoleonitrile

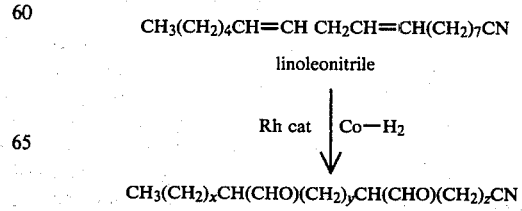

$$CH_3(CH_2)_xCH(CHO)(CH_2)_yCH(CHO)(CH_2)_zCN$$

-continued
where x + y + z = 14

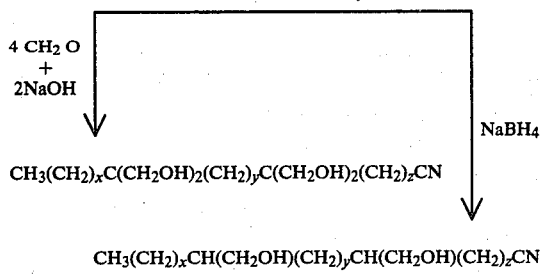

Likewise, linolenonitrile can be converted into the triformyl derivative by hydroformylation using a rhodium catalyst and synthesis gas. A tri [gem-bis(hydroxymethyl)]octadecanonitrile can be formed by reacting triformyl nitrile with excess formaldehyde and caustic.

In this invention, unsaturated fatty compounds having 14–24 carbon atoms and having the above terminal polar function can be used.

Similarly, 9,9(10,10)-bis(hydroxymethyl)-N,N-disubstituted octadecanamide can be obtained from oleic acid as a starting material as illustrated in the following scheme:

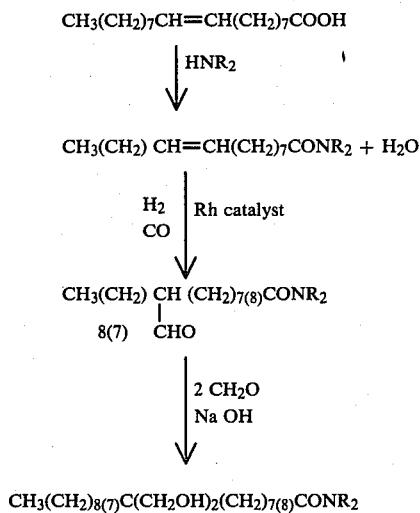

A 9,9(10,10)-bis(hydroxymethyl)N,N-disubstituted octadecanamide. The value of R in the disubstituted amide above for example can be dimethyl, diethyl, diphenyl, dibutyl, piperidene or morpholine. Again, where oleic acid is used as an example and non-conjugated linoleic and linolenic acids can be used as well as the unsaturated amides.

It is also been determined that one particular ester of oleic acid may be converted very usefully through the use of isobutylene to give the tertiary butyl ester denominated as t-butyl 9,9(10,10)-bis(hydroxymethyl) octadecanoate. The t-butyl esters of linolenic and linoleic acids are also employed.

Another class of compounds are noted as starting materials for containing the nitrile, amide or ester functionality which are reacted with synthesis gas to obtain the formyl group in more than one position in the molecule. In this case, oleic acid or oleyl alcohols are no longer sufficient and linoleyl or linolenyl acid or alcohol must be the starting material to ensure that there is more than one site of unsaturation. The formyl groups, which will be two or three according to the generic formula given herein, may be reduced with sodium borohydride to obtain, for instance, 9(10), 12(13) dihydroxymethyloctadecanonitrile, amide or the tertiary butyl ester of the starting acid.

It should be noted herein that the sum of m through t in the generic formula given in the Summary of the Invention, has a value of 11 through 19; that n plus q plus s are 1 through 3; n, q, and s are 0 or 1, preferably such that the sum of m through t is from 13 to 17 and that m and t are each 3 or greater. It is further preferred that m and t each have a value of 4, 5 or 6 or greater. It is also a preferred situation where q is 1 and n and s are each 0. It is again emphasized that at least two hydroxymethyl groups must be present on each molecule. This requirement may be satisfied by the two substituents being in a geminal configuration or by placing two hydroxymethyl groups on separate carbon atoms in the backbone. R is defined as an organic moiety which cause the amide to be tertiary. Suggested values for R are those having from 1 to 4 carbon atoms such as methyl, ethyl, propyl, butyl, secbutyl or compounds such as morpholine, piperidine, hydroxypropyl, hydroxyethyl or mixtures thereof.

To conduct the synthesis gas reaction, hydrogen and carbon monoxide are added in a closed vessel at temperatures of from 100 to 150 degrees C. The hydrogen and carbon monoxide may be maintained conveniently at from ratios of 1.5:0.5 to about 0.5:1.5 molar ratio to one another. It is noted that the ratio is not critical so long as the pressure is maintained in the reaction vessel by the component gases and that the amount of hydrogen is not so great as to substantially reduce the unsaturated starting materials.

In practice, the hydroformylation with the synthesis gas is conducted at from about 90 degrees C. to about 170 degrees C., preferably from 110 degrees C. to about 130 degrees C. Above the higher temperatures described above, increased amounts of unwanted by-products are formed in the reaction mixture. The pressure conditions are maintained in this sealed system at from about 20 to about 500 atmospheres, preferably from about 30 to about 100 atmospheres absolute during the hydroformylation.

Conventional cobalt catalyst may be employed to obtain a single formyl group, but it is not desired for the polyunsaturated compounds due to reduction of the unsaturation. Conveniently, however, the practical catalyst to use during the synthesis gas reaction is rhodium. The rhodium may be in any convenient form such as rhodium metal, rhodium oxide, and various other rhodium salts such as rhodium chloride, rhodium dicarbonyl chloride dimer, rhodium nitrate, rhodium trichloride and other similar materials. The rhodium catalyst is also best utilized with a ligand such as trisubstituted phosphine or trisubstituted phosphite. The term trisubstituted includes both alkyl and aryl compounds and the substituted compounds of alkyl and aryl compounds.

A particularly valuable ligand for the rhodium carbonyl hydride is triphenylphosphite or triphenylphosphine in that both compounds are particularly useful in minimizing migration of the double bond thereby avoiding a large number of isomers with respect to the formyl group. In general, triarylphosphines or triarylphosphites may be used for this purpose in the formation of the rhodium carbonylhydride ligand. In addition, the foregoing materials are extremely valuable in minimizing the undesired saturation of the double bond or the reduction of the formyl group.

As was previously noted, materials such as sodium borohydride may be utilized to reduce the formyl group to a hydroxymethyl group thereby obtaining desired compounds of the invention.

However, in most cases it is desirable to convert the formyl group via the Tollens' reaction completely to the gem-bis(hydroxymethyl) structure. Such is done by utilizing two moles of formaldehyde per formyl group and also utilizing a strong base as a reactant. Should it be desired from some reason, weak base and one mole formaldehyde may be used to obtain the hydroxymethyl formyl compound which may be utilized for various purposes including subsequent reduction of the formyl group to give the gem-bis(hydroxymethyl) variety of the claimed compounds.

In either case, excess amounts of formaldehyde due to its inexpensive nature are utilized up to 1.5 preferably up to 1.2 times the amount of formaldehyde actually required to obtain the hydroxymethyl formyl or the gem-bis(hydroxymethyl) compounds. A convenient manner of adding the formaldehyde and conducting the Tollens' reaction is by using a methanol solution of formaldehyde.

The strong bases which may be employed conveniently include sodium hydroxide, althrough potassium or calcium hydroxide may also be employed. The Tollens' reaction is conducted at a temperature of from about 0 degrees to about 100 degrees C., preferably from about 20 degrees C. to about 70 degrees C.

The compounds of the present invention are most likely to be utilized to form urethanes with polyisocyanates. A substantial advantage in the present invention is that polar groups introduced into the molecule enhance miscibility of the respective urethane forming components. Another significant advantage is the wetting ability of the polar groups which allow for the introduction of pigments such as organic or inorganic pigments including titanium dioxide, chrome yellow, calcium or barium Lithol, phthocyanines and oxide pigments thereby providing urethane coatings with a high pigment carrying capability.

The following are suggested embodiments of the present invention.

EXAMPLE I

Preparation of formyloctadecanonitrile (FON)

Into a 1 liter, 316 SS autoclave equipped with stirrer and heat exchange coil is placed 617 grams of olenitrile, 3.0 grams of 5 percent rhodium on aluminum (Englehardt Industries) and 3.2 grams of triphenylphosphite. The autoclave is flushed with nitrogen then pressurized with carbon monoxidehydrogen (1:1) to 1080 psig. The temperature is increased to 127–133 degrees C. and maintained from 3.3 hours with a CO—$H_2$ pressure of 970–1080 psig. At this point a GC analysis indicated complete reaction of olenitrile with the formation of FON. The reaction was cooled, the pressure vented and the product filtered. The yield of FON is 681. Rhodium is removed from the product by vacuum distillation.

EXAMPLE II

Preparation of gem-bis(hydroxymethyl)octadecanonitrile (BHMON)

Into a 3 liter, glass reaction flask is placed 762 grams (2.60 moles) of formyloctadecanonitrile, 321 grams (5.84 moles) of a 54.6 percent solution of formaldehyde in methanol (Methyl Formcel, a product of Celanese Chemical Company), and 6.6 milliliters of 40 percent solution of sodium hydroxide in water. The temperature of the system is maintained at 40 degrees C. for 36 minutes then increased to 50 degrees C.

Then a 40 percent solution of sodium hydroxide in water is added (25 minutes) at a rate of 5.3 milliliters/minutes until a total of 297 grams is added, including the 6.6 milliliters initially added. Temperature is maintained at 45–50 degrees C. throughout the addition and then held at 50 degrees C. for an additional 2 hours. The reaction mixture was cooled to 16 degrees C. and 27.9 grams of a 12 percent solution of sodium borohydride in 43 percent sodium hydroxide is added. The reaction temperature is maintained between 16–27 degrees C. for 20 minutes.

The reaction mixture is stripped under vacuum at 49 degrees to remove methanol and water. The residual product is washed at 54 degrees C. with 500 milliliters of water plus 100 milliliters of saturated sodium sulfate solution. The upper organic phase is separated and washed successively with 500 milliliters of 0.1 N sodium hydroxide solution and 4X with 500 milliliters portions of water. The product is finally dried in vacuum (1 mm Hg) at 70 degrees C. The yield of crude BHMON was 832 grams.

EXAMPLE III

Preparation of 9(10), 12(13)-diformyloctadecanonitrile

Hydroformylation of 9,12-linoleonitrile was carried out similar to conditions described in Example I, except that the CO—$H_2$ pressure is maintained at 2000 psig.

EXAMPLE IV

Preparation of 9(10), 12(13)-bis(hydroxymethyl)octadecanonitrile

Into a solution of 8.86 grams of 9(10), 12(13)-diformyloctadecanonitrile (containing about 47 percent 9(10)-formyloctadecanonitrile) in 8.3 grams of isopropyl alcohol at 25 degrees C. is added 0.77 grams of sodium borohydride over a period of 5 minutes. After 4 hours at 28 degrees, additional sodium borohydride (9.24 grams) is added. After 44 minutes the reaction is worked up by addition of 5 milliliters acetone, distillation of the volatiles in vacuo. The residue is dissolved in a mixture of ether-water and the ether layer is washed with water. Evaporation of the ether yielded 7.60 grams of 9(10), 12(13)-bis(hydroxymethyl)octadecanonitrile containing some 9(10)-hydroxymethyloctadecanonitrile. Identification of the products was made by I.R., NMR and GC-MS.

EXAMPLE IV

Preparation of 9(10), 12(13)-bis(hydroxymethyl)octadecanonitrile

Into a solution of 8.86 grams of 9(10), 12(13)-diformyloctadecanonitrile (containing about 47 percent 9(10)-formyloctadecanonitrile) in 8.3 grams of isopropyl alcohol at 25 degrees C. is added 0.77 grams of sodium borohydride over a period of 5 minutes. After 4 hours at 28 degrees, additional sodium borohydride (0.24 grams) is added. After 44 minutes the reaction is worked up by addition of 5 milliliters acetone and distillation of the volatiles in vacuo. The residue is dissolved in a mixture of ether-water and the ether layer is washed with water. Evaporation of the ether yielded 7.60 grams of 9(10), 12(13)-bis(hydroxymethyl)octadecanonitrile. Identification of the products is made by I.R., NMR and GC-MS.

EXAMPLE VI

Thermoplastic and thermosetting polymers are prepared as shown in the table.

TABLE I

| | NCO Terminated Prepolymer 1 equivalent | Curative 0.95 equivalent | Split tear (psi) |
|---|---|---|---|
| A. | BHON/PM 1000 4:1 MDI | BHON/80 1:2 | 1344 |
| B. | BHON/PM 1000 4:1 MDI | 1,4 BD/BHON/C-20 triol 8:2:1 | 1288 |

These products show exceptional split tear strength.

BHON is used to indicate 9(10) gem-bis(hydroxymethyl) octadecanonitrile. MDI is methylene diisocyanate and PM 1000 is PolyMeg 1000 a polyoxytetramethylene glycol. The ratios are in equivalents. BD indicates 1,4 butane diol and C-20 triol is 9(10) gem-bis(-hydroxymethyl) octadecanol. A is a thermoplastic elastomer and B is a thermosetting elastomer.

What is claimed is:

1. Polyhydroxymethyl compounds containing a polar group which have the formula:

$$CH_3(CH_2)_m[C(CH_2OH)X]_n(CH_2)_p[C(CH_2OH)X]_q(CH_2)_r[C(CH_2OH)X]_s(CH_2)_t CH_2M$$

and mixtures thereof wherein X is either hydrogen or hydroxymethyl but not mixtures thereof provided that there are at least two hydroxymethyl groups per molecule; n plus q plus s are integers the sum of which is from 1 to 3; n, q and s are 0 or 1; m through t are integers the sum of which is from 11 to 19; and M is CN.

2. The composition of claim 1 wherein m through t is 13 to 17.

3. The composition of claim 1 wherein q is 1 and n and s are each 0.

4. The composition of claim 1 wherein m and t are each 4 or greater.

5. The compound 9,9(10,10)-bis-(hydroxymethyl) octadecanonitrile.

6. The compound 9,9(10,10) 12,12(13,13) tetra(hydroxymethyl)octadecanonitrile.

7. The compound 9,9(10,10) 12,12(13,13), 15,15(16,16)-hexa(hydroxymethyl)octadecanonitrile.

8. The compound 9(10); 12(13) di(hydroxymethyl) octadecanonitrile.

9. The compound 9(10); 12(13); 15(16)tri(hydroxymethyl)octadecanonitrile.

* * * * *